(12) United States Patent
Coulombel

(10) Patent No.: US 12,151,016 B2
(45) Date of Patent: Nov. 26, 2024

(54) HAIR SHAPING PROCESS USING A COMPOSITION COMPRISING AT LEAST ONE SILICONE ACRYLIC COPOLYMER

(71) Applicant: L'OREAL, Paris (FR)

(72) Inventor: Stéphanie Coulombel, Saint-Ouen (FR)

(73) Assignee: L'OREAL, Paris (FR)

( * ) Notice: Subject to any disclaimer, the term of this patent is extended or adjusted under 35 U.S.C. 154(b) by 800 days.

(21) Appl. No.: 17/288,106

(22) PCT Filed: Oct. 24, 2019

(86) PCT No.: PCT/EP2019/079088
§ 371 (c)(1),
(2) Date: Apr. 23, 2021

(87) PCT Pub. No.: WO2020/084079
PCT Pub. Date: Apr. 30, 2020

(65) Prior Publication Data
US 2021/0378941 A1    Dec. 9, 2021

(30) Foreign Application Priority Data
Oct. 25, 2018    (FR) ...................................... 1859880

(51) Int. Cl.
*A61K 8/895* (2006.01)
*A45D 7/02* (2006.01)
*A61Q 5/06* (2006.01)

(52) U.S. Cl.
CPC ............... *A61K 8/895* (2013.01); *A45D 7/02* (2013.01); *A61Q 5/06* (2013.01); *A61K 2800/48* (2013.01); *A61K 2800/805* (2013.01)

(58) Field of Classification Search
CPC .................................................... A61K 8/895
See application file for complete search history.

(56) References Cited

U.S. PATENT DOCUMENTS

| 5,061,481 | A | 10/1991 | Suzuki et al. |
| 5,219,560 | A | 6/1993 | Suzuki et al. |
| 5,221,534 | A | 6/1993 | DesLauriers et al. |
| 7,942,937 | B2 | 5/2011 | Brun |
| 8,828,272 | B2 | 9/2014 | Arnaud et al. |
| 2001/0055580 | A1 | 12/2001 | Belli et al. |
| 2002/0055562 | A1 | 5/2002 | Butuc |
| 2006/0045895 | A1 | 3/2006 | Ferrari et al. |
| 2009/0151086 | A1 | 6/2009 | Brun |
| 2011/0094531 | A1 | 4/2011 | Abbas |
| 2015/0283060 | A1 | 10/2015 | Metten et al. |
| 2019/0254954 | A1 | 8/2019 | Jegou et al. |
| 2020/0268635 | A1 | 8/2020 | Jacques et al. |

FOREIGN PATENT DOCUMENTS

| CN | 101455622 B | 2/2013 |
| EP | 1084694 A1 | 3/2001 |
| EP | 1132076 A1 | 9/2001 |
| EP | 1862162 A1 | 12/2007 |
| EP | 2070516 A1 | 6/2009 |
| FR | 2816500 A1 | 5/2002 |
| FR | 3045376 A1 | 6/2017 |
| FR | 3052977 A1 | 12/2017 |
| JP | 2012-136464 A | 7/2012 |
| WO | 95/00108 A1 | 1/1995 |
| WO | 2014/095165 A2 | 6/2014 |
| WO | 2017/011627 A1 | 1/2017 |
| WO | 2017/109147 A1 | 6/2017 |
| WO | 2020/084078 A1 | 4/2020 |
| WO | 2020/084085 A1 | 4/2020 |

OTHER PUBLICATIONS

International Search Report and Written Opinion for counterpart Application No. PCT/EP2019/079088, dated Jan. 30, 2020.
International Search Report and Written Opinion for counterpart Application No. PCT/EP2019/079087, dated Jan. 20, 2020.
International Search Report and Written Opinion for counterpart Application No. PCT/EP2019/079096, dated Jan. 20, 2020.
Todd, Charles et al., "Volatile Silicone Fluids for Cosmetic Formulations," Cosmetics and Toiletries, vol. 91, Jan. 1976, pp. 29-32.
Anonymous, "DOW CORNING® 1501 Fluid Personal Care Product Information Typical Properties," XP055390610, Retrieved from the Internet: http://www.corquiven.com.ve/esp/PDS/SILICON_1501_Fluid.pdf [retrieved on Jul. 13, 2017].
Translation of Chinese Office Action for counterpart Application No. 201980068917.6, dated Sep. 28, 2022.
Translation of Chinese Office Action for counterpart Application No. 201980068992.2, dated Oct. 21, 2022.
Translation of Chinese Office Action for counterpart Application No. 201980069976.5, dated Nov. 1, 2022.

*Primary Examiner* — Benjamin J Packard
(74) *Attorney, Agent, or Firm* — The Marbury Law Group, PLLC

(57) ABSTRACT

The present invention relates to a process for shaping keratin fibers using a composition comprising at least one silicone acrylic copolymer.

19 Claims, No Drawings

HAIR SHAPING PROCESS USING A COMPOSITION COMPRISING AT LEAST ONE SILICONE ACRYLIC COPOLYMER

CROSS REFERENCE TO RELATED APPLICATION

This is a national stage application of PCT/EP2019/079088, filed internationally on Oct. 24, 2019, which claims priority to French Application No. 1859880, filed on Oct. 25, 2018, which are both incorporated by reference herein in their entireties.

The present invention relates to a process for shaping keratin fibers using a composition comprising at least one silicone acrylic copolymer.

Many noninvasive technologies now exist for satisfying styling needs. Styling products are usually used to construct and structure the hairstyle and to give it long-lasting hold. These compositions generally comprise one or more fixing film-forming polymers, in a cosmetically acceptable medium. These polymers allow the formation of a coating film on the hair, or the formation of micro-welds between the individual hairs, thus ensuring the hairstyle hold.

Styling products are generally in the form of lacquers, mousses or gels. In particular, styling gels are often used in order to obtain strong fixing of the hairstyle. Styling gels are solutions of one or more fixing film-forming polymers, thickened or gelled with one or more thickening polymers.

However, the effects provided by these technologies disappear during the first shampoo wash and it is necessary to reapply them in order to obtain the desired effect. This imposes a more or less long and tedious routine on the consumer. For example, for a blow-drying product for frizzy hair, after applying the styling spray, the product needs to be distributed uniformly over the entire head of hair followed by performing blow-drying, which may take from 5 to 45 minutes depending on the desired result.

In contrast, long-lasting shape products allow the structure of the fiber to be definitively modified by breaking (reducing) the disulfide bonds which impose the original shape of the hair, followed by re-bridging (e.g.: oxidation of the cysteines to cystine after a mechanical action such as the insertion of curlers in the case of permanent waving). These products must, however, be reapplied at the root once hair regrowth occurs in order to conserve a uniform result. The results are irreversible and sensitize the hair. The superposition of relaxing products, for example, may cause discomfort and, in the long term, lead to real degradation of the fiber which may go as far as breakage.

The object of a semi-permanent styling product is to offer satisfaction as regards the durability of the styling effects after one or more shampoo washes, while at the same time preserving the integrity of the fiber so as to offer the consumer timesaving and improved safety. The term "styling effect" means performance in terms of manageability, provision of body, curl definition, volume control, sheen, case of shaping by natural drying, blow-drying and/or drying using flat tongs, and hairsetting. Ideally, it is also expected of this type of product that it be readily removable by means of an action or by a composition acting as a makeup remover.

Furthermore, the product must not generate any static electricity.

There is thus a need to formulate a treatment, especially a treatment which provides coating on the treated fiber, which satisfies the following criteria:

being adherent to the fiber and remaining perceptible after several shampoo washes,
allowing the hair to be easily and durably shaped,
affording good cosmetic qualities,
being easy to use, without any risk of damaging the hair,
being compatible with conventionally used hair treatments (shampooing, hair conditioning, dying), but also compatible with sebum.

It has now been discovered that the use of a composition containing at least one silicone acrylic copolymer, optionally combined with the use of a heating tool, for example a hair dryer or a straightening iron, makes it possible to generate coating around the hair fiber, which is persistent with respect to shampooing, and which provides the desired styling properties, while at the same time being friendly to the fiber. What is more, this coating is persistent with respect to shampooing. Furthermore, this composition applied according to this process has good working qualities, notably in terms of distribution on the head of hair, while at the same time giving the hair good cosmetic properties, notably in terms of disentangling of wet and dry hair, and strand separation.

In addition, the composition according to this process allows the shampoo washes to be spaced apart by limiting the regreasing of the treated hair, gives better volume control, reduces the frizziness and affords a gain in manageability.

A subject of the invention is thus, notably, a process for shaping keratin fibers, notably the hair, comprising the following steps:
  i. applying to the keratin fibers a composition comprising at least one silicone acrylic copolymer as defined below, and
  ii. applying heat to the keratin fibers using a heating tool, the application of heat possibly taking place during or after the application of the composition, preferably after.

It has been observed that the fibers thus treated have a shampoo-resistant coating which makes it possible notably to improve the shaping of the hair, notably in terms of gain in volume and volume persistence, and in terms of curl definition. In addition, the composition used in the process has good working qualities on application (distribution) and after shampoo washing (disentangling of wet and dry hair, strand separation).

For the purposes of the present invention, the term "shampoo-resistant coating" means that the shaping obtained persists after one shampoo wash, preferably after three shampoo washes, more preferentially after five shampoo washes.

Other features, aspects, objects and advantages of the present invention will emerge even more clearly on reading the description and the examples that follow.

The invention is not limited to the examples illustrated. The features of the various examples may notably be combined within variants which are not illustrated.

In the following text, and unless otherwise indicated, the limits of a range of values are included in that range, notably in the expressions "between" and "ranging from . . . to . . . ".

Moreover, the expression "at least one" used in the present description is equivalent to the expression "one or more".

According to the present application, the term "keratin fibers" denotes human keratin fibers and more particularly the hair.

1. Composition

The process according to the invention comprises a step of applying to keratin fibers a composition, notably a shaping composition.

The composition according to the invention is preferably a cosmetic composition for shaping keratin fibers, in particular human keratin fibers such as the hair.

1.1. Silicone Acrylic Copolymer

The shaping composition used in the process according to the invention comprises at least one silicone acrylic copolymer.

Preferably, the copolymer according to the invention is water-insoluble. For the purposes of the present invention, the term "water-insoluble" refers to a compound that is insoluble in water at ordinary temperature (25° C.) and at atmospheric pressure (760 mmHg or $1.013 \times 10^5$ Pa) (solubility of less than 5% by weight, preferably 1% by weight and even more preferentially 0.1% by weight).

The shaping composition comprises at least one silicone acrylic copolymer, comprising at least the following units:
  a) a polydimethylsiloxane unit, the polydimethylsiloxane unit comprising at least one polymerizable radical group on each of the two ends of the chain, and
  b) an alkyl acrylate or methacrylate unit, preferably at least two alkyl acrylate or methacrylate units, the alkyl radical comprising from 1 to 30 carbon atoms, preferentially from 1 to 22 carbon atoms, better still 1 to 10 carbon atoms, and more preferentially 2 to 6 carbon atoms.

For the purposes of the present invention, the term "alkyl acrylate or methacrylate unit" means a unit derived from an alkyl acrylate or methacrylate monomer.

For the purposes of the present invention, the term "alkyl radical" means a linear or branched hydrocarbon-based radical, which is saturated or comprises one or more conjugated or non-conjugated unsaturations.

The term "polydimethylsiloxanes" (also abbreviated as PDMSs) denotes, in accordance with what is generally accepted, any organosilicon polymer or oligomer of linear structure, of variable molecular weight, obtained by polymerization and/or polycondensation of suitably functionalized silanes, and constituted essentially of a repetition of main units in which the silicon atoms are linked together via oxygen atoms (siloxane bond $\equiv$Si—O—Si$\equiv$), comprising methyl radicals directly linked via a carbon atom to said silicon atoms.

The PDMS chains which can be used to obtain the copolymer used according to the invention comprise at least one polymerizable radical group, preferably located on at least one of the ends of the chain, that is to say that the PDMS can, for example, have a polymerizable radical group on each of the two ends of the chain or have a polymerizable radical group on one end of the chain and a trimethylsilyl end group on the other end of the chain.

A polymerizable radical group is understood to mean a radical capable of polymerizing with other polymerizable radical groups or monomers.

Preferably, the polymerizable radical group is an acrylic or methacrylic group containing from 1 to 6 carbon atoms, more preferentially a $CH_2$=CH—COO-$\{$ group.

The copolymers used in the composition are generally obtained according to the usual methods of polymerization and grafting, for example by radical polymerization of a polyalkylsiloxane including at least one polymerizable radical group (for example on one of the ends of the chain or on both ends) and of at least one acrylic or methacrylic monomer, such as acrylic acid, methacrylic acid or an ester thereof, as described, for example, in the documents U.S. Pat. No. 5,061,481 and US-A-5 219 560.

More particularly, the silicone acrylic copolymer comprises at least the following units:
  a) a polydimethylsiloxane (PDMS) unit including at least one polymerizable radical group on each of the two ends of the chain chosen from an acrylic or methacrylic group containing from 1 to 6 carbon atoms, more preferentially a $CH_2$—CH—COO-$\{$ group; and
  b) a $C_1$-$C_{30}$, preferably $C_1$-$C_{22}$, preferentially $C_1$-$C_{10}$ and better still $C_2$-$C_6$ alkyl acrylate or methacrylate unit.

Even more particularly, the shaping composition of use in the process according to the invention comprises at least one silicone acrylic copolymer comprising at least the following units:
  a) a polydimethylsiloxane (PDMS) unit including at least one polymerizable radical group on each of the two ends of the chain chosen from a $CH_2$—CH—COOA-$\{$ group, where A represents an alkyl group comprising from 1 to 3 carbon atoms; and
  b) a $C_1$-$C_{22}$, preferably $C_1$-$C_{10}$ and better still $C_2$-$C_6$ alkyl acrylate or methacrylate unit.

More particularly still, the silicone acrylic copolymer according to the invention is a copolymer with the INCI name isobutyl methacrylate/bis-hydroxypropyl dimethicone acrylate copolymer, such as for example the compound sold by Grant Industries under the name Granacrysil BMAS.

It is an isobutyl methacrylate/bis-hydroxypropyl dimethicone acrylate copolymer in solution in isododecane.

The silicone acrylic copolymer(s) may be present in a total amount ranging from 0.01% to 25% by weight, preferably from 0.1% to 20% by weight, more preferentially from 0.5% to 15% by weight and better still from 1% to 10% by weight relative to the total weight of the shaping composition.

1.2. Fatty Substance

The composition may comprise one or more fatty substances.

The term "fatty substance" is intended to mean an organic compound that is insoluble in water at ordinary temperature (25° C.) and at atmospheric pressure (760 mmHg or $1.013 \times 10^5$ Pa) (solubility of less than 5% and preferably of less than 1%, more preferably still of less than 0.1%). They bear in their structure at least one hydrocarbon-based chain comprising at least 6 carbon atoms or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

The fatty substances of the invention do not contain any salified carboxylic acid groups.

In addition, the fatty substances of the invention are not (poly)oxyalkylenated or (poly)glycerolated ethers.

More particularly, the fatty substance(s) are chosen from $C_6$-$C_{16}$ hydrocarbons, hydrocarbons containing more than 16 carbon atoms, non-silicone oils of animal origin, triglycerides of plant or synthetic origin, fluoro oils, fatty alcohols, esters of fatty acids and/or of fatty alcohols other than triglycerides and non-silicone waxes, in particular plant waxes, non-silicone waxes, and silicones other than the silicone acrylic copolymers described previously, and mixtures thereof.

The term "oil" is intended to mean a "fatty substance" that is liquid at ambient temperature (25° C.) and at atmospheric pressure (760 mmHg or $1.013 \times 10^5$ Pa).

The term "non-silicone oil" is intended to mean an oil not containing any silicon (Si) atoms and the term "silicone oil" is intended to mean an oil containing at least one silicon atom.

It is recalled that the fatty alcohols, esters and acids more particularly contain at least one saturated or unsaturated, linear or branched hydrocarbon-based group, comprising 6 to 30 and better still from 8 to 30 carbon atoms, which is optionally substituted, in particular, with one or more hydroxyl groups (in particular 1 to 4). If they are unsaturated, these compounds may comprise one to three conjugated or unconjugated carbon-carbon double bonds.

As regards the $C_6$-$C_{16}$ hydrocarbons, they are more particularly linear, branched or optionally cyclic, and are preferably alkanes. Examples that may be mentioned include hexane, cyclohexane, undecane, dodecane, tridecane or isoparaffins, such as isohexadecane, isodecane or isododecane, and mixtures thereof.

The linear or branched hydrocarbons of mineral or synthetic origin containing more than 16 carbon atoms are preferably chosen from liquid paraffins, petroleum jelly, liquid petroleum jelly, polydecenes and hydrogenated polyisobutene such as Parleam®, and mixtures thereof.

A hydrocarbon-based oil of animal origin that may be mentioned is perhydrosqualene.

The triglycerides of plant or synthetic origin are preferably chosen from liquid fatty acid triglycerides including from 6 to 30 carbon atoms, for instance heptanoic or octanoic acid triglycerides, or alternatively more particularly from those present in plant oils, for instance sunflower oil, corn oil, soybean oil, marrow oil, grapeseed oil, sesame oil, hazelnut oil, apricot oil, macadamia oil, arara oil, castor oil, avocado oil, jojoba oil, shea butter oil and synthetic caprylic/capric acid triglycerides, for instance those sold by the company Stearineries Dubois or those sold under the names Miglyol® 810, 812 and 818 by the company Dynamit Nobel, and mixtures thereof.

Fluoro oils that may be mentioned include perfluoromethylcyclopentane and perfluoro-1,3-dimethylcyclohexane, sold under the names Flutec® PCI and Flutec® PC3 by the company BNFL Fluorochemicals; perfluoro-1,2-dimethylcyclobutane; perfluoroalkanes such as dodecafluoropentane and tetradecafluorohexane, sold under the names PF 5050 ® and PF 5060 ® by the company 3M, or alternatively bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052 ® by the company 3M.

The fatty alcohols that are suitable for use in the invention are more particularly chosen from linear or branched, saturated or unsaturated alcohols comprising from 6 to 30 carbon atoms and preferably from 8 to 30 carbon atoms. Examples that may be mentioned include cetyl alcohol, isostearyl alcohol, stearyl alcohol and a mixture thereof (cetylstearyl alcohol), octyldodecanol, 2-butyloctanol, 2-hexyldecanol, 2-undecylpentadecanol, oleyl alcohol, linolenyl alcohol, ricinolcyl alcohol, undecylenyl alcohol and linoleyl alcohol, and mixtures thereof.

As regards the esters of fatty acids and/or fatty alcohols advantageously other than the triglycerides mentioned above and non-silicone waxes, mention may be made especially of esters of saturated or unsaturated, linear $C_1$-$C_{26}$ or branched $C_3$-$C_{26}$ aliphatic monoacids or polyacids and of saturated or unsaturated, linear $C_1$-$C_{26}$ or branched $C_3$-$C_{26}$ aliphatic monoalcohols or polyalcohols, the total carbon number of the esters being greater than or equal to 6 and more advantageously greater than or equal to 10.

Among the monoesters, mention may be made of dihydroabietyl behenate; octyldodecyl behenate; isocetyl behenate; cetyl lactate; C12-C15 alkyl lactate; isostearyl lactate; lauryl lactate; linoleyl lactate; oleyl lactate; (iso) stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononanoate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate, and mixtures thereof.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ and $C_1$-$C_{26}$ di-, tri-, tetra- or pentahydroxy alcohols may also be used.

Mention may be made in particular of: diethyl sebacate; diisopropyl sebacate; diisopropyl adipate; di-n-propyl adipate; dioctyl adipate; diisostearyl adipate; dioctyl malcate; glyceryl undecylenate; octyldodecyl stearoyl stearate; pentaerythrityl monoricinoleate; pentaerythrityl tetraisononanoate; pentacrythrityl tetrapelargonate; pentacrythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononate; and polyethylene glycol distearates, and mixtures thereof.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate, dioctyl malate, hexyl laurate, 2-hexyldecyl laurate, isononyl isononanoate and cetyl octanoate, and mixtures thereof.

The composition may also comprise, as fatty ester, sugar esters and diesters of $C_6$-$C_{30}$ and preferably $C_{12}$-$C_{22}$ fatty acids. It is recalled that the term "sugar" is intended to mean oxygen-bearing hydrocarbon-based compounds bearing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose, glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant may also be chosen from mono-, di-, tri- and tetraesters, polyesters, and mixtures thereof.

These esters may be, for example, oleates, laurates, palmitates, myristates, behenates, cocoates, stearates, linoleates, linolenates, caprates and arachidonates, or mixtures thereof such as, in particular, oleopalmitate, oleostearate and palmitostearate mixed esters.

More particularly, use is made of monoesters and diesters and especially sucrose, glucose or methylglucose monooleate or diolcate, stearate, behenate, oleopalmitate, linoleate, linolenate or oleostearate.

An example that may be mentioned is the product sold under the name Glucate® DO by the company Amerchol, which is a methylglucose dioleate.

Examples of esters or mixtures of esters of sugar and of fatty acid that may also be mentioned include:
the products sold under the names F160, F140, F110, F90, F70 and SL40 by the company Crodesta, respectively denoting sucrose palmitate/stearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
the products sold under the name Ryoto Sugar Esters, for example referenced B370 and corresponding to sucrose behenate formed from 20% monoester and 80% diester-triester-polyester;
the sucrose mono-dipalmito-stearate sold by the company Goldschmidt under the name Tegosoft® PSE.

The non-silicone wax(es) are chosen in particular from carnauba wax, candelilla wax, esparto wax, paraffin wax, ozokerite, plant waxes, such as olive tree wax, rice wax, hydrogenated jojoba wax and absolute flower waxes, such as the blackcurrant blossom essential wax sold by Bertin (France), and animal waxes, such as beeswaxes or modified beeswaxes (cerabellina); other waxes or waxy raw materials that may be used according to the invention are in particular marine waxes, such as that sold by Sophim under the reference M82, polyethylene waxes or polyolefin waxes in general.

The silicones, other than the silicone acrylic copolymers described previously, that may be used in the cosmetic composition of the present invention are volatile or non-volatile, cyclic, linear or branched silicones, which are unmodified or modified with organic groups, having a viscosity from $5 \times 10^{-6}$ to 2.5 m$^2$/s at 25° C., and preferably $1 \times 10^5$ to 1 m$^2$/s.

The silicones that may be used in accordance with the invention may be in the form of oils, waxes, resins or gums, preferably silicone oils.

Preferably, the silicone is chosen from polydialkylsiloxanes, especially polydimethylsiloxanes (PDMSs), and organomodified polysiloxanes comprising at least one functional group chosen from poly(oxyalkylene) groups, amino groups and alkoxy groups.

Organopolysiloxanes are defined in greater detail in Walter Noll's Chemistry and Technology of Silicones (1968), Academic Press. They may be volatile or non-volatile.

When they are volatile, the silicones are more particularly chosen from those with a boiling point of between 60° C. and 260° C., and even more particularly from:
cyclic polydialkylsiloxanes including from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Silicone Volatile® FZ 3109 sold by Union Carbide, of formula:

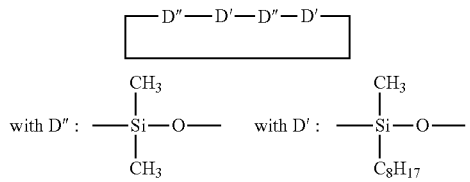

Mention may also be made of mixtures of cyclic polydialkylsiloxanes with organosilicon compounds, such as the mixture of octamethylcyclotetrasiloxane and tetra(trimethylsilyl) pentaerythritol (50/50) and the mixture of octamethylcyclotetrasiloxane and oxy-1,1'-bis(2,2,2',2',3,3'-hexatrimethylsilyloxy) neopentane;

(ii) linear volatile polydialkylsiloxanes containing 2 to 9 silicon atoms and having a viscosity of less than or equal to $5 \times 10^6$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, "Volatile Silicone Fluids for Cosmetics".

Non-volatile polydialkylsiloxanes, polydialkylsiloxane gums and resins, polyorganosiloxanes modified with the above organofunctional groups, and mixtures thereof, are preferably used.

These silicones are more particularly chosen from polydialkylsiloxanes, among which mention may be made mainly of polydimethylsiloxanes bearing trimethylsilyl end groups. The viscosity of the silicones is measured at 25° C. according to ASTM standard 445 Appendix C.

Among these polydialkylsiloxanes, mention may be made, in a non-limiting manner, of the following commercial products:
the Silbione® oils of the 47 and 70 047 series or the Mirasil® oils sold by Rhodia, for instance the oil 70 047 V 500 000;
the oils of the Mirasil® series sold by the company Rhodia;
the oils of the 200 series from Dow Corning, such as DC200, with a viscosity of 60 000 mm$^2$/s;
the Viscasil® oils from General Electric and certain oils of the SF series (SF 96, SF 18) from General Electric.

Mention may also be made of polydimethylsiloxanes bearing dimethylsilanol end groups, known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are polydi(C$_1$-C$_{20}$)alkylsiloxanes.

The silicone gums that may be used in accordance with the invention are especially polydialkylsiloxanes and preferably polydimethylsiloxanes with high number-average molecular weights of between 200 000 and 1 000 000, used alone or as a mixture in a solvent. This solvent may be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products that may be used more particularly in accordance with the invention are mixtures such as:

mixtures formed from a polydimethylsiloxane with a hydroxy-terminated chain, or dimethiconol (CTFA), and from a cyclic polydimethylsiloxane, also known as cyclomethicone (CTFA), such as the product Q2 1401 sold by the company Dow Corning;

mixtures of a polydimethylsiloxane gum and a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;

mixtures of two PDMSs with different viscosities, and more particularly of a PDMS gum and a PDMS oil, such as the product SF 1236 from General Electric. The product SF 1236 is a mixture of a gum SE 30 defined above with a viscosity of 20 $m^2/s$ and of an oil SF 96 with a viscosity of $5\times10^6$ $m^2/s$. This product preferably comprises 15% of gum SE 30 and 85% of an oil SF 96.

The organopolysiloxane resins that may be used in accordance with the invention are crosslinked siloxane systems containing the following units:

$R_2SiO_{2/2}$, $R_3SiO_{1/2}$, $RSiO_{3/2}$ and $SiO_{4/2}$, in which R represents an alkyl containing 1 to 16 carbon atoms. Among these products, the ones that are particularly preferred are those in which R denotes a $C_1$-$C_4$ lower alkyl group, more particularly methyl.

Among these resins, mention may be made of the product sold under the name Dow Corning 593 or those sold under the names Silicone Fluid SS 4230 and SS 4267 by the company General Electric, which are silicones of dimethyl/trimethylsiloxane structure.

Mention may also be made of the trimethyl siloxysilicate-type resins sold especially under the names X22-4914, X21-5034 and X21-5037 by Shin-Etsu.

The organomodified silicones that may be used in accordance with the invention are silicones as defined above and including in their structure one or more organofunctional groups attached via a hydrocarbon-based group.

Besides the silicones described above, the organomodified silicones may be polydiarylsiloxanes, in particular polydiphenylsiloxanes, and polyalkylarylsiloxanes functionalized by the organofunctional groups mentioned previously.

The polyalkylarylsiloxanes are particularly chosen from linear and/or branched polydimethyl/methylphenylsiloxanes and polydimethyl/diphenylsiloxanes with a viscosity ranging from $1\times10^{-5}$ to $5\times10^{-2}$ $m^2/s$ at 25° C.

Among these polyalkylarylsiloxanes, examples that may be mentioned include the products sold under the following names:

the Silbione® oils of the 70 641 series from Rhodia;
the oils of the Rhodorsil® 70 633 and 763 series from Rhodia;
the oil Dow Corning 556 Cosmetic Grade Fluid from Dow Corning;
the silicones of the PK series from Bayer, such as the product PK20;
the silicones of the PN and PH series from Bayer, such as the products PN1000 and PH1000;
certain oils of the SF series from General Electric, such as SF 1023, SF 1154, SF 1250 and SF 1265.

Among the organomodified silicones, mention may be made of polyorganosiloxanes comprising:

polyethyleneoxy and/or polypropyleneoxy groups optionally including $C_6$-$C_{24}$ alkyl groups, such as the products known as dimethicone copolyol sold by the company Dow Corning under the name DC 1248 or the oils Silwet® L 722, L 7500, L 77 and L 711 by the company Union Carbide, and the $(C_{12})$alkylmethicone copolyol sold by the company Dow Corning under the name Q2 5200;

substituted or unsubstituted amino groups, such as the products sold under the names GP 4 Silicone Fluid and GP 7100 by the company Genesee or the products sold under the names Q2 8220 and Dow Corning 929 or 939 by the company Dow Corning. The substituted amino groups are, in particular, $C_1$-$C_4$ aminoalkyl groups;

alkoxylated groups such as the product sold under the name Silicone Copolymer F-755 by SWS Silicones, and Abil Wax® 2428, 2434 and 2440 by the company Goldschmidt.

The fatty substance(s) are advantageously chosen from hydrocarbons containing more than 16 carbon atoms, C6-C16 alkanes, triglycerides or oils of plant origin, liquid synthetic triglycerides, fatty alcohols, esters of fatty acids and/or of fatty alcohols other than triglycerides and nonsilicone waxes, or mixtures thereof.

Preferably, the shaping composition according to the invention comprises one or more fatty substances chosen from saturated hydrocarbons including a carbon number of between 8 and 16, more preferentially from isododecane, isohexadecane and/or mixtures thereof.

Preferably, the shaping composition comprises isododecane and/or isohexadecane; more preferentially, the composition according to the invention comprises isododecane.

According to a particular embodiment, the isododecane sold under the reference Isododecane by Incos is used.

The shaping composition according to the invention may comprise one or more fatty substances present in a total amount ranging from 0.1% to 95% by weight, preferably from 1% to 95% by weight and better still from 5% to 92% by weight relative to the total weight of the composition.

In a particular variant of the invention, the composition comprises one or more fatty substances in a total amount ranging from 0.1% to 30% by weight, preferably from 1% to 20% by weight and better still from 5% to 10% by weight relative to the total weight of the composition.

1.3. Organic Solvents

The composition may comprise one or more organic solvents, different from the fatty substances described previously.

More particularly, the organic solvents are chosen from linear or branched and preferably saturated monoalcohols or diols, comprising from 2 to 10 carbon atoms, such as ethyl alcohol, isopropyl alcohol, hexylene glycol (2-methyl-2,4-pentanediol), neopentyl glycol and 3-methyl-1,5-pentanediol; aromatic alcohols such as benzyl alcohol and phenylethyl alcohol; glycols or glycol ethers, for instance ethylene glycol monomethyl, monoethyl and monobutyl ethers, propylene glycol or ethers thereof, for instance propylene glycol monomethyl ether, butylene glycol or dipropylene glycol; and also diethylene glycol alkyl ethers, especially of $C_1$-$C_4$, for instance diethylene glycol monoethyl ether or monobutyl ether, alone or as a mixture.

Preferably, linear or branched, preferably saturated, monoalcohols or diols, comprising from 2 to 10 carbon atoms are preferred, more preferentially monoalcohols comprising from 2 to 10 carbon atoms, and more particularly ethanol is preferred.

Preferably, the composition according to the invention comprises one or more organic solvents other than fatty substances, preferentially one or more monoalcohols comprising from 2 to 10 carbon atoms; better still, the composition according to the invention comprises ethanol.

When they are present, the organic solvents other than fatty substances usually represent from 1% to 99% by weight, more preferentially from 10% to 95% by weight, preferably from 50% to 93% by weight and better still from 70% to 90% by weight, relative to the total weight of the composition.

Preferably, the composition that is useful in the process according to the invention is noncoloring.

For the purposes of the present invention, the term "noncoloring composition" refers to a composition which does not comprise any pigments or dyes intended to color keratin fibers, in particular the hair.

The term "pigment" is intended to denote a white or colored solid particle which is naturally insoluble in the hydrophilic and lipophilic liquid phases usually employed in cosmetics or which is rendered insoluble by formulation in the form of a lake, where appropriate. More particularly, the pigment has little or no solubility in aqueous-alcoholic media.

The term "composition not comprising any dyes" refers more precisely to a composition which does not comprise any direct dye or oxidation dye precursor (oxidation base and coupler) or any other compound which, by reaction, gives a colored species in the composition or on the fibers, usually used for coloring human keratin fibers.

The noncoloring composition according to the invention is preferably free of pigment and dye, or, if it comprises at least one pigment and/or at least one dye, their total content does not exceed 0.005% by weight relative to the weight of the composition. Specifically, at such a content, only the composition would be dyed, i.e. no dyeing effect would be observed on the keratin fibers.

It is recalled that oxidation dye precursors, oxidation bases and couplers are colorless or sparingly colored compounds, which, via a condensation reaction in the presence of an oxidizing agent, give a colored species. With regard to direct dyes, these compounds are colored and have a certain affinity for keratin fibers.

1.4. Film-Forming Polymer

The composition may notably comprise one or more film-forming polymers other than the silicone acrylic polymer(s) described previously.

For the purposes of the invention, the term "polymer" refers to a compound corresponding to the repetition of one or more units (these units being derived from compounds known as monomers). This or these unit(s) are repeated at least twice and preferably at least three times.

The term "film-forming polymer" is intended to mean a polymer capable of forming, by itself alone or in the presence of an auxiliary film-forming agent, a macroscopically continuous film on a support, in particular on keratin materials, and preferably a cohesive film.

Among the film-forming polymers that may be used in the composition of the present invention, mention may be made of synthetic polymers, of free-radical type or of polycondensate type, and polymers of natural origin, and mixtures thereof. Film-forming polymers that may be mentioned in particular include acrylic polymers, polyurethanes, polyesters, polyamides, polyureas and cellulose-based polymers, for instance nitrocellulose.

The acrylic film-forming polymers that may be used according to the invention may result from the polymerization of at least one ethylenically unsaturated monomer chosen from ethylenic carboxylic acids, esters thereof and amides thereof. Unsaturated ethylenic carboxylic acids that may be used include acrylic acid, methacrylic acid, crotonic acid, maleic acid and itaconic acid. (Meth)acrylic acid and crotonic acid are preferably used, and more preferably (meth)acrylic acid. The esters of these carboxylic acids may be chosen from (meth)acrylic acid esters (also known as (meth)acrylates), notably alkyl (meth)acrylates, in particular $C_1$-$C_{30}$ and preferably $C_1$-$C_{20}$ alkyl (meth)acrylates, aryl (meth)acrylates, in particular $C_6$-$C_{10}$ aryl (meth)acrylates, and hydroxyalkyl (meth)acrylates, in particular $C_2$-$C_6$ hydroxyalkyl (meth)acrylates. Among the alkyl (meth)acrylates that may be mentioned are methyl methacrylate, ethyl methacrylate, butyl methacrylate, isobutyl methacrylate, 2-ethylhexyl methacrylate, lauryl methacrylate and cyclohexyl methacrylate. Mention may be made, among hydroxyalkyl (meth)acrylates, of hydroxyethyl acrylate, 2-hydroxypropyl acrylate, hydroxyethyl methacrylate or 2-hydroxypropyl methacrylate. Needless to say, it is possible to use a mixture of these monomers. The (meth)acrylic acid esters which are particularly preferred are the alkyl (meth)acrylates. According to the present invention, the alkyl group may be either fluorinated or perfluorinated, i.e. some or all of the hydrogen atoms of the alkyl group are substituted with fluorine atoms.

Examples of amides of said carboxylic acids that may be mentioned include (meth)acrylamides, and notably N-alkyl (meth)acrylamides, in particular of a $C_2$-$C_{12}$ alkyl. Among the N-alkyl (meth)acrylamides that may be mentioned are N-ethylacrylamide, N-butylacrylamide, N-octylacrylamide and N-undecylacrylamide.

The acrylic film-forming polymer that may be used according to the invention may comprise, in addition to the monomers mentioned previously, at least one styrene monomer, such as styrene or α-methylstyrene.

As acrylic polymer synthesized with a styrene compound, mention may be made of the styrene/acrylate(s) copolymers (INCI name) sold under the name Joncryl 77 by the company BASF, under the name Yodosol GH41F by the company AkzoNobel, or the styrene/acrylates/ammonium methacrylate copolymers (INCI name) sold under the name Syntran 5760 CG by the company Interpolymer.

The composition of use according to this process according to the invention may comprise an acrylic cationic copolymer, comprising at least the units obtained from the following monomers:
 a) monomer derived from acrylic or methacrylic esters or amides and including at least one cationic group, and
 b) alkyl acrylate or methacrylate monomer, the alkyl radical comprises from 1 to 30 carbon atoms, preferably 1 to 22 carbon atoms, better still 1 to 10 carbon atoms and preferentially 2 to 6 carbon atoms.

For the purposes of the present invention, the term cationic compound or group means a compound or group bearing a permanent cationic charge or a charge obtained by protonation of a (cationizable) function, such as an amine function, by the protons of the medium.

Preferably, the copolymer according to the invention is water-insoluble. For the purposes of the present invention, the term "water-insoluble" refers to a compound that is insoluble in water at ordinary temperature (25° C.) and at atmospheric pressure (760 mmHg or $1.013 \times 10^5$ Pa) (solubility of less than 5%, preferably 1% and even more preferentially 0.1%).

Preferentially, the cationic acrylic copolymer contains c) at least a third unit obtained from a polymerizable ethylenic monomer, preferably from a monomer having the following formula:

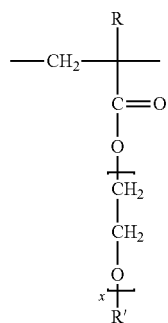
(A')

in which R and R', which may be identical or different, represent a hydrogen atom, a $C_1$-$C_{10}$ and preferably $C_1$-$C_4$ alkyl radical; preferably, R is a methyl radical; better still, R is a methyl radical and R' is an ethyl radical;

x ranging from 1 to 10, preferably from 1 to 3, and better still x is 1.

More particularly, the cationic acrylic copolymer present in the composition according to the invention comprises at least units obtained from the following two lists of monomers:

a) monomer derived from acrylic or methacrylic esters or amides and including at least one cationic group, having the following formulae:

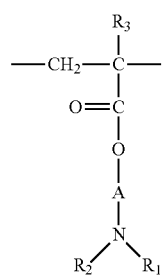
(I)

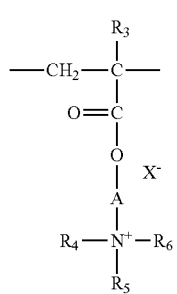
(II)

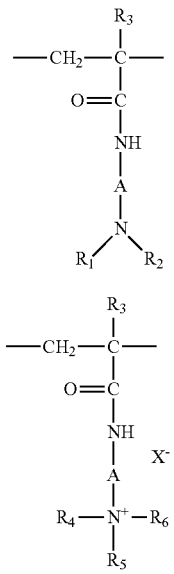
(III)

(IV)
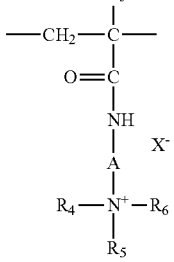

in which:
R$_3$, which may be identical or different, denote a hydrogen atom or a CH$_3$ group;
A, which may be identical or different, represent a linear or branched divalent alkyl group of 1 to 6 carbon atoms, preferably 2 or 3 carbon atoms, or a hydroxyalkyl group of 1 to 4 carbon atoms;
R$_4$, R$_5$ and R$_6$, which may be identical or different, represent an alkyl group containing from 1 to 18 carbon atoms or a benzyl group, and preferably an alkyl group containing from 1 to 6 carbon atoms;
R$_1$ and R$_2$, which may be identical or different, represent a hydrogen atom or an alkyl group containing from 1 to 6 carbon atoms, and preferably methyl or ethyl;
X$^-$ denotes an anion derived from a mineral or organic acid, such as a methosulfate anion or a halide such as chloride or bromide,
b) $C_1$-$C_{30}$, preferably $C_1$-$C_{22}$, preferentially $C_1$-$C_{10}$ and better still $C_2$-$C_6$ alkyl acrylate or methacrylate monomer.

Even more preferentially, the cationic acrylic copolymer, optionally present in the composition according to the invention, comprises at least the units obtained from the following monomers:
a) monomer derived from acrylic or methacrylic esters or amides and including at least one cationic group, having the following formulae:

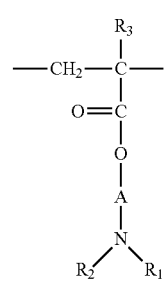
(I)

-continued

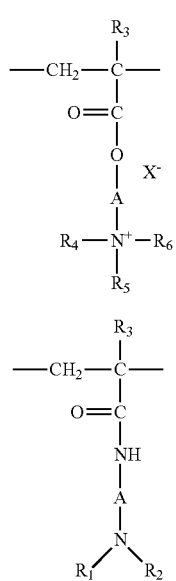
(II)

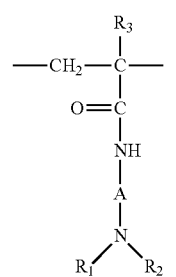
(III)

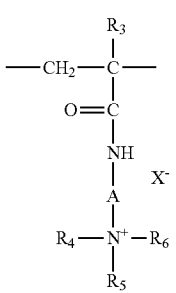
(IV)

in which:
- R₃, which may be identical or different, denote a hydrogen atom or a CH₃ group;
- A, which may be identical or different, represent a linear or branched divalent alkyl group of 1 to 6 carbon atoms, preferably 2 or 3 carbon atoms, or a hydroxyalkyl group of 1 to 4 carbon atoms;
- R₄, R₅ and R₆, which may be identical or different, represent an alkyl group containing from 1 to 18 carbon atoms or a benzyl group, and preferably an alkyl group containing from 1 to 6 carbon atoms;
- R₁ and R₂, which may be identical or different, represent a hydrogen atom or an alkyl group containing from 1 to 6 carbon atoms, and preferably methyl or ethyl;
- X⁻ denotes an anion derived from a mineral or organic acid, such as a methosulfate anion or a halide such as chloride or bromide, preferably, formulae (I) and (II)

b) C₁-C₃₀, preferably C₁-C₂₂, preferentially C₁-C₁₀ and better still C₂-C₆ alkyl acrylate or methacrylate monomer and c) polymerizable ethylenic monomer, preferably from a monomer having the following formula

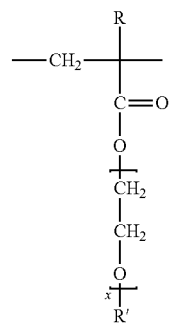
(A')

in which R and R', which may be identical or different, represent a hydrogen atom, a C₁-C₁₀ and preferably C₁-C₄ alkyl radical; preferably, R is a methyl radical; better still, R is a methyl radical and R' is an ethyl radical;

x ranging from 1 to 10, preferably from 1 to 3, and better still x is 1.

Even more particularly, the composition of use in the process according to the invention may comprise at least one copolymer comprising at least the units obtained from the following monomers:
- a) a monomer derived from acrylic or methacrylic esters of formula (I) or (II) as described previously, preferably of formula (II),
- b) a C₁-C₂₂, preferably C₁-C₁₀ and better still C₂-C₆ alkyl acrylate or methacrylate monomer,
- c) a monomer of formula (A') as described previously.

Most particularly, the composition may comprise one or more cationic acrylic copolymers, which are preferably water-insoluble, bearing the following units:
- a) methacryloyloxyethyltrimethylammonium salt,
- b) butyl methacrylate, and
- c) ethoxyethyl methacrylate.

Such copolymers are described, for example, in JP5745266. Preferably, the polymer contains the preceding three monomers in the following proportions relative to the total number of monomer units, by weight in the constituted copolymer, without taking into account the salts thereof:
- a) in a proportion of 0.5% to 20%, preferably between 1% and 5%;
- b) in a proportion of 20% to 98%, preferably between 40% and 97%; and
- c) in a proportion of 1.5% to 95%, preferably between 2% and 55%.

Preferably, the copolymer is not amphoteric, i.e. it does not comprise any units bearing an anionic charge.

Preferably, the units of the copolymer are all methacrylate derivatives.

Even more particularly, the copolymer corresponds to the copolymer whose INCI name is Polyquaternium-99, for instance the polymer sold by the company GOO-Chemical under the name Plascize L-514.

It is the butyl methacrylate/ethoxyethyl methacrylate/methacryloyloxyethyltrimethylammonium chloride copolymer, at 30% in ethanol:

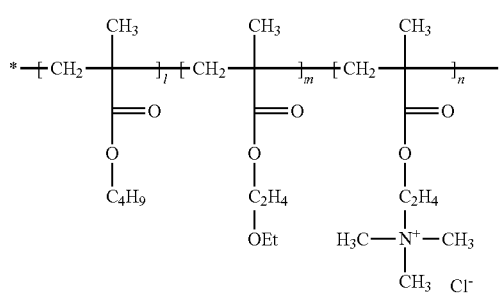

According to a particular embodiment, the composition according to the invention comprises one or more film-forming polymers chosen from cationic, anionic, amphoteric and nonionic film-forming polymers and/or mixtures thereof.

According to a preferred embodiment, the film-forming polymers are chosen from cationic and anionic film-forming polymers, and mixtures thereof.

According to a preferred embodiment, the cationic and/or anionic film-forming polymers are chosen from acrylic film-forming polymers.

According to a particularly preferred embodiment, the cationic film-forming polymers are chosen from polymers corresponding to the INCI name Polyquaternium-99 and the anionic film-forming polymers are chosen from polymers corresponding to the INCI name styrene/acrylates/ammonium methacrylate copolymer.

When it is (they are) present in the composition of use in the process according to the invention, the film-forming copolymer(s) other than the silicone acrylic copolymer(s) are in a total content ranging from 0.01% to 15% by weight relative to the total weight of the composition, preferably from 0.1% to 10% by weight and more preferentially from 1% to 8% by weight, relative to the total weight of the composition.

1.5. Thickener

The composition may notably comprise one or more mineral or organic thickeners.

The mineral thickeners are preferably chosen from organophilic clays and fumed silicas, or mixtures thereof.

The organophilic clay may be chosen from montmorillonite, bentonite, hectorite, attapulgite and sepiolite, and mixtures thereof. The clay is preferably a bentonite or a hectorite.

These clays may be modified with a chemical compound chosen from quaternary amines, tertiary amines, amine acetates, imidazolines, amine soaps, fatty sulfates, alkylaryl sulfonates and amine oxides, and mixtures thereof.

Mention may be made, as organophilic clays, of quaternium-18 bentonites, such as those sold under the names Bentone 3, Bentone 38 and Bentone 38V by Rheox, Tixogel VP by United Catalyst and Claytone 34, Claytone 40 and Claytone XL by Southern Clay; stearalkonium bentonites, such as those sold under the names Bentone 27 by Rheox, Tixogel LG by United Catalyst and Claytone AF and Claytone APA by Southern Clay; and quaternium-18/benzalkonium bentonites, such as those sold under the names Claytone HT and Claytone PS by Southern Clay.

The fumed silicas may be obtained by high-temperature hydrolysis of a volatile silicon compound in an oxyhydrogen flame, producing a finely divided silica. This process makes it possible in particular to obtain hydrophilic silicas bearing a large number of silanol groups at their surface. Such hydrophilic silicas are sold, for example, under the names Aerosil 130®, Aerosil 200®, Aerosil 255®, Aerosil 300® and Aerosil 380® by Degussa and Cab-O-Sil HS-5®, Cab-O-Sil EH-5®, Cab-O-Sil LM-130®, Cab-O-Sil MS-55® and Cab-O-Sil M-5® by Cabot.

It is possible to chemically modify the surface of the silica via chemical reaction in order to reduce the number of silanol groups. It is notably possible to substitute silanol groups with hydrophobic groups: a hydrophobic silica is then obtained.

The hydrophobic groups may be:
trimethylsiloxyl groups, which are obtained in particular by treating fumed silica in the presence of hexamethyldisilazane. Silicas thus treated are known as Silica silylate according to the CTFA (6th Edition, 1995). They are sold, for example, under the references Aerosil R812® by Degussa and Cab-O-Sil TS-530® by Cabot.
dimethylsilyloxyl or polydimethylsiloxane groups, which are obtained in particular by treating fumed silica in the presence of polydimethylsiloxane or dimethyldichlorosilane. Silicas thus treated are known as Silica dimethyl silylate according to the CTFA (6th Edition, 1995). They are sold, for example, under the references Aerosil R972® and Aerosil R974® by the company Degussa and Cab-O-Sil TS-610® and Cab-O-Sil TS-720® by the company Cabot.

The fumed silica preferably has a particle size that may be nanometric to micrometric, for example ranging from about 5 to 200 nm.

Preferably, the composition comprises a hectorite, an organomodified bentonite or an optionally modified fumed silica.

The composition may also comprise one or more organic thickeners.

These thickeners may be chosen from fatty acid amides (coconut monoethanolamide or diethanolamide, oxyethylenated carboxylic acid monoethanolamide alkyl ether), polymeric thickeners such as cellulose-based (ethylcellulose, hydroxyethylcellulose, hydroxypropylcellulose or thickeners carboxymethylcellulose), guar gum and derivatives thereof (hydroxypropyl guar), gums of microbial origin (xanthan gum, scleroglucan gum), acrylic acid or acrylamidopropanesulfonic acid crosslinked homopolymers and associative polymers (polymers comprising hydrophilic regions and fatty-chain hydrophobic regions (alkyl or alkenyl containing at least 10 carbon atoms) that are capable, in an aqueous medium, of reversibly combining with each other or with other molecules).

According to a particular embodiment, the organic thickener is chosen from a hydrocarbon-based block copolymer, preferably a block copolymer that is soluble or dispersible in a liquid fatty phase.

The hydrocarbon-based block copolymer may especially be a diblock, triblock, multiblock, radial or star copolymer, or mixtures thereof.

For the purposes of the invention, the term "hydrocarbon-based polymer" refers to a polymer constituted solely of carbon and hydrogen atoms.

Such hydrocarbon-based block copolymers are described in patent application US-A-2002/005 562 and in patent U.S. Pat. No. 5,221,534.

The copolymer may contain at least one block whose glass transition temperature is preferably less than 20° C., preferably less than or equal to 0° C., preferably less than or equal to −20° C. and more preferably less than or equal to −40° C. The glass transition temperature of said block may be between −150° C. and 20° C. and especially between 100° C. and 0° C.

The hydrocarbon-based block copolymer present in the composition according to the invention is a copolymer formed by polymerization of an olefin. The olefin may especially be an ethylenically unsaturated monomer.

Examples of olefins that may be mentioned include ethylenic carbide monomers, especially containing one or two ethylenic unsaturations and containing from 2 to 5 carbon atoms, such as ethylene, propylene, butadiene, isoprene or pentadiene. Advantageously, the hydrocarbon-based block copolymer is a block copolymer of styrene and olefin.

Block copolymers comprising at least one styrene block and at least one block comprising units chosen from butadiene, ethylene, propylene, butylene and isoprene or a mixture thereof are especially preferred.

According to one preferred embodiment, the hydrocarbon-based block copolymer is hydrogenated to reduce the residual ethylenic unsaturations after the polymerization of the monomers.

In particular, the hydrocarbon-based block copolymer is a copolymer, optionally hydrogenated, containing styrene blocks and ethylene/$C_3$-$C_4$ alkylene blocks. Diblock copolymers, which are preferably hydrogenated, that may be mentioned include styrene-ethylene/propylene copolymers, styrene-ethylene/butadiene copolymers and styrene-ethylene/butylene copolymers. Diblock polymers are notably sold under the name Kraton® G1701E by the company Kraton Polymers. Triblock copolymers, which are preferably hydrogenated, that may be mentioned include styrene-ethylene/propylene-styrene copolymers, styrene-ethylene/butadiene-styrene copolymers, styrene-ethylene/butylene-styrene copolymers, styrene-isoprene-styrene copolymers and styrene-butadiene-styrene copolymers. Triblock polymers are notably sold under the names Kraton® G1650, Kraton® G1652, Kraton® D1101, Kraton® D1102 and Kraton® D1160 by the company Kraton Polymers.

According to one embodiment of the present invention, the hydrocarbon-based block copolymer is a styrene-ethylene/propylene diblock copolymer, notably such as the diblock polymers sold under the name Kraton® G1701E by the company Kraton Polymers.

According to one particular embodiment, the organic thickener is chosen from cellulose-based thickeners (ethylcellulose, hydroxyethylcellulose, hydroxypropylcellulose or carboxymethylcellulose), guar gum and derivatives thereof (hydroxypropyl guar), gums of microbial origin (xanthan gum or scleroglucan gum) and crosslinked acrylic acid or acrylamidopropanesulfonic acid homopolymers, and preferably from cellulose-based thickeners in particular with ethylcellulose or hydroxyethylcellulose.

According to one embodiment, the thickener(s) are preferably organic, and more preferentially the thickener(s) are chosen from polymers, better still from cellulose-based thickeners and/or hydrocarbon-based block copolymers, and/or mixtures thereof.

The total content of thickener(s), if they are present, usually ranges from 0.01% to 20% by weight, relative to the weight of the composition, preferably from 0.1% to 10% by weight and better still from 1% to 8% by weight relative to the total weight of the composition.

1.6. Additives

The composition of use in the process according to the invention may comprise one or more additives usually used in cosmetics, chosen, for example, from surfactants, cationic polymers other than the polymers described previously, pH agents, reducing agents, softeners, antifoams, moisturizers, UV-screening agents, peptizers, solubilizers, fragrances, proteins, vitamins, and mixtures thereof.

Needless to say, a person skilled in the art will take care to select this or these optional additional compound(s) such that the advantageous properties intrinsically associated with the composition according to the invention are not, or are not substantially, adversely affected by the envisaged addition(s).

Preferably, when the composition comprises one or more additives, the total amount of additive(s) ranges from 0.01% to 50% by weight, more preferentially from 0.1% to 45% by weight and better still from 1% to 35% by weight, relative to the total weight of the composition.

The composition used in the process according to the invention may notably be in the form of a suspension, a dispersion, a gel, an emulsion, notably an oil-in-water (O/W) or water-in-oil (W/O) emulsion, or a multiple emulsion (W/O/W or polyol/O/W or O/W/O), in the form of a wax, a paste, a cream, a mousse, a stick, a spray (pump and aerosol), a lotion, a dispersion of vesicles, notably of ionic or nonionic lipids, or a two-phase or multi-phase lotion. Preferably, the composition is in the form of a gel.

A person skilled in the art may select the appropriate presentation form, and also the method for preparing it, on the basis of his general knowledge, taking into account firstly the nature of the constituents used, especially their solubility in the support, and secondly the intended application of the composition.

The composition of the invention may be anhydrous or aqueous. The composition is preferably anhydrous.

For the purposes of the present invention, the term "anhydrous composition" means that the water content is less than 2% by weight and preferably less than 1% by weight, and better still the composition is free of water.

The composition may be applied to wet or dry hair, preferentially wet hair.

According to a particular embodiment of the process of the invention, the fibers are washed before applying the composition described above.

According to a particular embodiment, the composition may in particular be applied at the roots.

The bath ratio of the composition applied to the hair (weight ratio between the amount of composition applied and the amount of hair) may be between 0.05 and 10, and more particularly between 0.05 and 5.

The hair is optionally rinsed and/or wrung out in order to remove an excess of composition.

The process comprises a step of applying heat (or heating step).

Heating Step

The step of applying heat may take place during or after the step of applying the composition. Preferably, the step of applying heat takes place after the application of the composition. An optional leave-on time may take place between the application of the composition and the application of heat.

According to one embodiment, a rinsing step may take place after the step of applying the composition. According to a preferred embodiment, the step of applying the composition is not followed by a rinsing step.

The step of applying heat may be performed using any heating device.

One or more heating tools may be applied individually or successively to the hair.

The application of heat may be performed for a time of between 2 seconds and 1 hour and preferentially between 2 seconds and 1 minute.

The application of the heating means may take place by successive touches or by sliding the appliance along the fibers.

The heating tool may be a straightening iron, a curling iron, a crimping iron, a waving iron, a hood, a hairdryer, an infrared heating system or heating curlers.

Preferably, the heating tool is a straightening iron or a hairdryer. Preferably, the process according to the invention uses a step of applying heat by means of a straightening iron.

During the step of applying heat to the keratin fibers, a mechanical action may be exerted on the locks, such as combing, brushing or running the fingers through.

The application of heat may be performed at a temperature of between 30° C. and 230° C., preferentially between 80° C. and 230° C. and more preferentially between 100° C. and 230° C.

When the step of applying heat to the keratin fibers is performed using a hood or a hairdryer, the temperature is between 30° C. and 110° C., preferably between 50° C. and 90° C.

During step (b2), the passage of the straightening or curling iron, preferably the straightening iron, may be performed at a temperature ranging from 110° C. to 230° C., preferably between 140° C. and 230° C.

According to a preferred embodiment, the process involves a step of applying heat by means of a hairdryer (drying) and a step of applying heat by means of a straightening iron. Preferably, the process involves a step of applying heat by means of a hairdryer (drying) followed by a step of applying heat by means of a straightening iron. The present invention will now be described more specifically by means of examples, which do not in any way limit the scope of the invention. However, the examples make it possible to support specific characteristics, variants and preferred embodiments of the invention.

EXAMPLES

1. Preparation of the Compositions

Compositions A to G according to the invention and the comparative composition H were prepared using the ingredients whose contents are indicated in the table below as weight percentages of starting material relative to the total weight of the composition.

|  | A | B | C | D | E | F | G | H |
|---|---|---|---|---|---|---|---|---|
| Silicone acrylic copolymer (containing 40% by weight active material in isododecane) (1) | 12.5 (5 am) | 8.75 (3.5 am) | 12.5 (5 am) | 8.75 (3.5 am) | 12.5 (5 am) | 12.5 (5 am) | 8.75 (3.5 am) | — |
| Styrene/ethylene-propylene diblock copolymer (2) | — | — | — | 5 | — | — | — | — |
| Ethyl cellulose | — | — | — | — | — | 2 | — | — |
| Styrene/acrylates/ammonium methacrylate copolymer (3) | — | — | — | — | — | — | 10 | — |
| Isohexadecane | qs 100% | — | — | — | — | — | — | — |
| Isododecane | — | — | — | qs 100% | qs 100% | — | — | qs 100% |
| Ethanol | — | qs 100% | qs 100% | — | — | qs 100% | qs 100% | — |

(1) Granacrysil BMAS, sold by the company Grant Industries.
(2) Kraton, G1701 EU SQR 1111 sold by the company Kraton Polymers.
(3) Syntran 5760 CG, sold by the company Interpolymer.

When the step of applying heat to the keratin fibers is performed using a straightening iron, the temperature is between 110° C. and 230° C., preferably between 140° C. and 230° C.

In a particular variant, the process of the invention involves a step (b1) of applying heat using a hood or a hairdryer, preferably a hairdryer, and a step (b2) of applying heat using a straightening or curling iron, preferably a straightening iron.

Preferably, step (b1) is performed before step (b2).

During step (b1), also referred to as the drying step, the fibers may be dried, for example at a temperature above or equal to 30° C. According to a particular embodiment, this temperature is above 40° C. According to a particular embodiment, this temperature is above 45° C. and below 110° C.

Preferably, if the fibers are dried, they are dried, in addition to a supply of heat, with a flow of air. This flow of air during drying makes it possible to improve the strand separation of the coating.

During drying, a mechanical action may be exerted on the locks, such as combing, brushing or running the fingers through.

2. Application Protocols

The protocols for application (to locks of hair, malleable heads or models) were as follows:

| Protocol according to the invention | Comparative protocol |
|---|---|
| Shampooing | Shampooing |
| Application of the composition onto wet straight or curly natural hair | Applying the composition to wet, straight or curly natural hair |
| Predrying with a hairdryer or blow-drying | Drying naturally |
| Straightening iron (3 passes at the roots at 210° C.) | |

3. Evaluation and Results

The evaluation protocol after drying relates to the evaluation of the impact on the shape, the cosmetic criteria (feel) and the appearance criteria (macroscopic effects, SEM visualization).

The shampoo-persistence evaluation protocol is as follows. Performance of several cycles:

Wetting of the hair

Shampooing

Rinsing

Drying with a hairdryer

Evaluation of the impact on the shape, the cosmetic criteria (feel) and the appearance criteria (macroscopic effects, SEM visualization).

3.1 Appearance of Locks by SEM

Observations by scanning electron microscope (SEM) demonstrate the surface state of treated hair, on the day of application and after shampoo washing, and reveal the quality of the coating formed by the polymer and its persistence.

The evaluated locks of hair lead to the following observations (application of 0.4 g of composition/g of hair).

With composition A according to the invention and by following the protocol according to the invention, homogeneous, uniform and covering coating of the fiber was observed. This coating is persistent for up to five shampoo washes. This coating is thicker and more uniform when the heating tool used is the straightening iron. The same effects are observed with composition B, with persistence of the coating to up to three shampoo washes.

With composition A according to the invention and according to the comparative protocol, fine and non-uniform, irregular coating in the form of aggregates was observed. Furthermore, the deposit is only very sparingly persistent on the fiber. Thus, heat allows better distribution and better adhesion of the polymer to the fiber, which affords the persistence of the effects on shampooing.

3.2 Cosmetic Aspects 3.2.1. Volume-Evaluation on Malleable Heads

Malleable heads are provided for this test. Each of the compositions C and D was applied to these malleable heads. The compositions are applied per half-head, i.e. on the right or left side of the head of hair separated by a line in the middle, at a rate of 4 g per half-head. The effects thereof are compared with the other half-head on which only water is applied in the same amounts. By following the protocol according to the invention (shampooing, applying the formulation to wet hair and to the roots, predrying with a hairdryer and treating the roots three times with a straightening iron at 210° C.), a gain in volume is observed, with persistence for up to three shampoo washes for the half-heads treated with each of the compositions C and D.

3.2.2. Volume-Evaluation by Consumers and Professionals

An evaluation of composition D was also performed in terms of gain in volume and of volume persistence after several shampoo washes after applying this composition by consumers and professionals. The test was performed by 6 hairstylists and 24 consumers with fine hair. By following the protocol according to the invention (shampooing, applying formulation D to wet hair and to the roots, predrying using a hairdryer and treating the roots three times with a straightening iron at 210° C.), a gain in volume is observed, with an immediate effect and with persistence for up to three shampoo washes.

3.2.3. Curls-Evaluation on Locks

Composition E according to the invention was applied according to the protocol according to the invention (shampooing, applying the formulation to wet hair at a rate of 0.15 g of composition/g of hair, predrying using a hairdryer and treating the entire length of the locks three times with a straightening iron at 210° C.), on locks of type IV curly hair. Its efficiency was compared with control locks treated only with isododecane, composition H, applied in the same amount. Better curl definition was observed, with persistence for up to five shampoo washes for the hair treated with composition E.

The invention claimed is:

1. A process for shaping keratin fibers comprising:
   i. applying to the keratin fibers a composition comprising at least one silicone acrylic copolymer, wherein the silicone acrylic copolymer comprises at least the following units:
      a) a polydimethylsiloxane unit, the polydimethylsiloxane unit including at least one polymerizable radical group on each of two ends of the unit, and
      b) an alkyl acrylate or methacrylate unit comprising from 1 to 30 carbon atoms, and
   ii. applying heat to the keratin fibers using a heating tool, the application of heat taking place before, during or after the application of the composition,
   wherein the composition does not comprise pigments or dyes to color the keratin fibers.

2. The process of claim 1, wherein the silicone acrylic copolymer comprises at least the following units:
   a) a polydimethylsiloxane (PDMS) unit including at least one polymerizable radical group on each of the two ends of the chain chosen from an acrylic or methacrylic group containing from 1 to 6 carbon atoms; and
   b) a $C_1$-$C_{30}$ alkyl acrylate or methacrylate unit.

3. The process of claim 1, wherein the silicone acrylic copolymer comprises at least the following units:
   a) a polydimethylsiloxane (PDMS) unit including at least one polymerizable radical group on each of the two ends of the chain chosen from a $CH_2$=CH—COOA-§ group, where A represents an alkyl group comprising from 1 to 3 carbon atoms; and
   b) a $C_1$-$C_{22}$ alkyl acrylate or methacrylate unit.

4. The process of claim 1, wherein the composition comprises the silicone acrylic copolymer(s) in a total amount ranging from about 0.01% to about 25% by weight, relative to the total weight of the composition.

5. The process of claim 1, wherein the composition comprises the silicone acrylic copolymer(s) in a total amount ranging from about 1% to about 10% by weight, relative to the total weight of the composition.

6. The process of claim 1, wherein the composition comprises one or more fatty substances.

7. The process of claim 1, wherein the composition comprises one or more fatty substances chosen from saturated hydrocarbons including a carbon number of between 8 and 16 and/or mixtures thereof.

8. The process of claim 1, wherein the composition comprises the fatty substance(s) in a total content ranging from about 0.1% to about 95% by weight, relative to the total weight of the composition.

9. The process of claim 1, wherein the composition comprises the fatty substance(s) in a total content ranging from about 5% to about 92% by weight, relative to the total weight of the composition.

10. The process of claim 1, wherein the composition comprises one or more film-forming polymers other than the silicone acrylic copolymer, chosen from cationic, anionic, amphoteric, or nonionic film-forming polymers, or mixtures thereof.

11. The process of claim 1, wherein the composition comprises one or more cationic and/or anionic acrylic film-forming polymers other than the silicone acrylic copolymer.

12. The process of claim 10, wherein the composition comprises the film-forming polymer(s) in a total amount ranging from about 0.01% to about 15% by weight, relative to the total weight of the composition.

13. The process of claim 10, wherein the composition comprises the film-forming polymer(s) in a total amount ranging from about 1% to about 8% by weight, relative to the total weight of the composition.

14. The process of claim 1, wherein the composition comprises one or more thickeners chosen from mineral and organic thickeners and/or mixtures thereof.

15. The process of claim 14, wherein the composition comprises the thickener(s) in a total amount ranging from about 0.01% to about 20% by weight, relative to the total weight of the composition.

16. The process of claim 1, wherein the composition comprises one or more organic solvents other than fatty substances.

17. The process of claim 1, wherein the step of applying heat to the keratin fibers using a heating tool is performed at a temperature of between 30° C. and 230° C.

18. The process of claim 1, wherein the heating tool is chosen from one or more of a straightening iron, a curling iron, a crimping iron, a waving iron, a hood, a hairdryer, an infrared heating system, or heating curlers.

19. The process of claim 1, wherein applying heat takes place after applying the composition.

* * * * *